United States Patent
Searcy et al.

(10) Patent No.: US 10,556,999 B2
(45) Date of Patent: Feb. 11, 2020

(54) PURIFICATION AND DECOLORIZATION OF POLYMERS

(71) Applicant: TOLMAR, Inc., Fort Collins, CO (US)

(72) Inventors: Justin Drew Searcy, Vista, CA (US); George Sal Lewis, Hewitt, NJ (US); John Charles Middleton, Fort Collins, CO (US)

(73) Assignee: Tolmar, Inc., Fort Collins, CO (US)

( * ) Notice: Subject to any disclaimer, the term of this patent is extended or adjusted under 35 U.S.C. 154(b) by 0 days.

(21) Appl. No.: 16/071,636

(22) PCT Filed: Jan. 26, 2017

(86) PCT No.: PCT/US2017/015095
§ 371 (c)(1),
(2) Date: Jul. 20, 2018

(87) PCT Pub. No.: WO2017/132350
PCT Pub. Date: Aug. 3, 2017

(65) Prior Publication Data
US 2019/0016860 A1     Jan. 17, 2019

Related U.S. Application Data

(60) Provisional application No. 62/288,782, filed on Jan. 29, 2016.

(51) Int. Cl.
| | |
|---|---|
| C08F 2/46 | (2006.01) |
| C08F 2/50 | (2006.01) |
| C08G 61/04 | (2006.01) |
| C08J 3/28 | (2006.01) |
| C08F 6/06 | (2006.01) |
| C08F 6/02 | (2006.01) |
| C08G 63/90 | (2006.01) |
| C08F 6/12 | (2006.01) |
| C08F 6/00 | (2006.01) |
| A61K 47/34 | (2017.01) |
| B01J 19/12 | (2006.01) |
| B01J 21/06 | (2006.01) |
| B01J 35/00 | (2006.01) |
| C08G 83/00 | (2006.01) |

(52) U.S. Cl.
CPC ............... *C08J 3/28* (2013.01); *A61K 47/34* (2013.01); *B01J 19/123* (2013.01); *B01J 21/063* (2013.01); *B01J 35/004* (2013.01); *C08F 6/006* (2013.01); *C08F 6/02* (2013.01); *C08F 6/06* (2013.01); *C08F 6/12* (2013.01); *C08G 63/90* (2013.01); *C08G 83/004* (2013.01); *B01J 2219/0877* (2013.01); *B01J 2219/0892* (2013.01); *B01J 2219/1203* (2013.01); *C08J 2367/04* (2013.01)

(58) Field of Classification Search
CPC ........ C08J 3/28; C08J 2367/04; B01J 21/063; B01J 2219/0892; B01J 35/004; B01J 19/123; B01J 2219/0877; B01J 2219/1203; A61L 47/34
USPC .......................................... 522/148, 1; 520/1
See application file for complete search history.

(56) References Cited

U.S. PATENT DOCUMENTS

| | | | |
|---|---|---|---|
| 5,779,912 | A | 7/1998 | Gonzalez-Martin et al. |
| 2002/0028911 | A1 | 3/2002 | Barnette et al. |
| 2004/0092393 | A1 | 5/2004 | Bygott et al. |
| 2006/0091067 | A1 | 5/2006 | Fan et al. |
| 2007/0142495 | A1* | 6/2007 | Neffgen ............... A61K 6/0017 523/116 |
| 2008/0081877 | A1* | 4/2008 | Liu ......................... C08F 6/02 525/191 |
| 2009/0082196 | A1 | 3/2009 | Tanaka et al. |
| 2014/0088210 | A1* | 3/2014 | Yorde ...................... C08J 11/04 521/48 |

FOREIGN PATENT DOCUMENTS

| | | |
|---|---|---|
| EP | 0469520 | 2/1992 |
| EP | 1147812 | 10/2001 |
| EP | 0816413 | 6/2005 |
| WO | WO 01/17679 | 3/2001 |
| WO | WO 2013/058838 | 4/2013 |
| WO | WO 2014/097309 | 6/2014 |

OTHER PUBLICATIONS

International Search Report issued by the U.S. Patent and Trademark Office for International Patent Application No. PCT/US2017/015095, dated Apr. 28, 2017, 3 pages.
Written Opinion issued by the U.S. Patent and Trademark Office for International Patent Application No. PCT/US2017/015095, dated Apr. 28, 2017, 8 pages.
International Preliminary Report on Patentability for International (PCT) Patent Application No. PCT/US2017/015095, dated Aug. 9, 2018 10 pages.
Bahnemann et al. "Titanium dioxide-mediated photocatalysed degradation of few selected organic pollutants in aqueous suspensions," Catalysis Today, Jun. 2007, vol. 124, No. 3-4, pp. 133-148.
Bakardjieva et al. "Photoactivity of anatase-rutile TiO2 nanocrystalline mixtures obtained by heat treatment of homogeneously precipitated anatase," Applied Catalysis B: Environmental, Jun. 2005, vol. 58, No. 3-4, pp. 193-202.

(Continued)

*Primary Examiner* — Jessica Whiteley
(74) *Attorney, Agent, or Firm* — Sheridan Ross P.C.

(57) ABSTRACT

Methods according to the present invention decolorize a polymer by mixing a solution of the polymer with a photocatalyst and exposing the mixture to ultraviolet light; by way of non-limiting example, the polymer may be a star polymer and the photocatalyst may be titanium dioxide. Methods according to the present invention also utilize a metal scavenger, in some embodiments a solid-phase metal scavenger, to remove a metal catalyst from a polymer solution; by way of non-limiting example, the metal catalyst may be a tin catalyst. The decolorization methods and the catalyst removal methods of the present invention may be practiced separately, sequentially in any order, or simultaneously.

18 Claims, 1 Drawing Sheet

(56) References Cited

OTHER PUBLICATIONS

Carp et al. "Photoinduced reactivity of titanium dioxide," Progress in Solid State Chemistry, 2004, vol. 32, No. 1-2, pp. 33-177.
Fujishima et al. "Titanium dioxide photocatalysis," Journal of Photochemistry and Photobiology C: Photochemistry Reviews, Jun. 2000, vol. 1, No. 1, pp. 1-21.
Gaya et al. "Heterogeneous photocatalytic degradation of organic contaminants over titanium dioxide: A review of fundamentals, progress and problems," Journal of Photochemistry and Photobiology C: Photochemistry Reviews, Mar. 2008, vol. 9, No. 1, pp. 1-12.
Hurum et al. "Explaining the Enhanced Photocatalytic Activity of Degussa P25 Mixed-Phase TiO2 Using EPR," The Journal of Physical Chemistry B, May 15, 2003, vol. 107, No. 19, pp. 4545-4549.
Ohtani et al. "What is Degussa (Evonik) P25? Crystalline composition analysis, reconstruction from isolated pure particles and photocatalytic activity test," Journal of Photochemistry and Photobiology A: Chemistry, Dec. 2010, vol. 216, No. 2-3, pp. 179-182.
Extended Search Report for European Patent Application No. 17744884.2, dated Jul. 29, 2019 8 pages.

\* cited by examiner

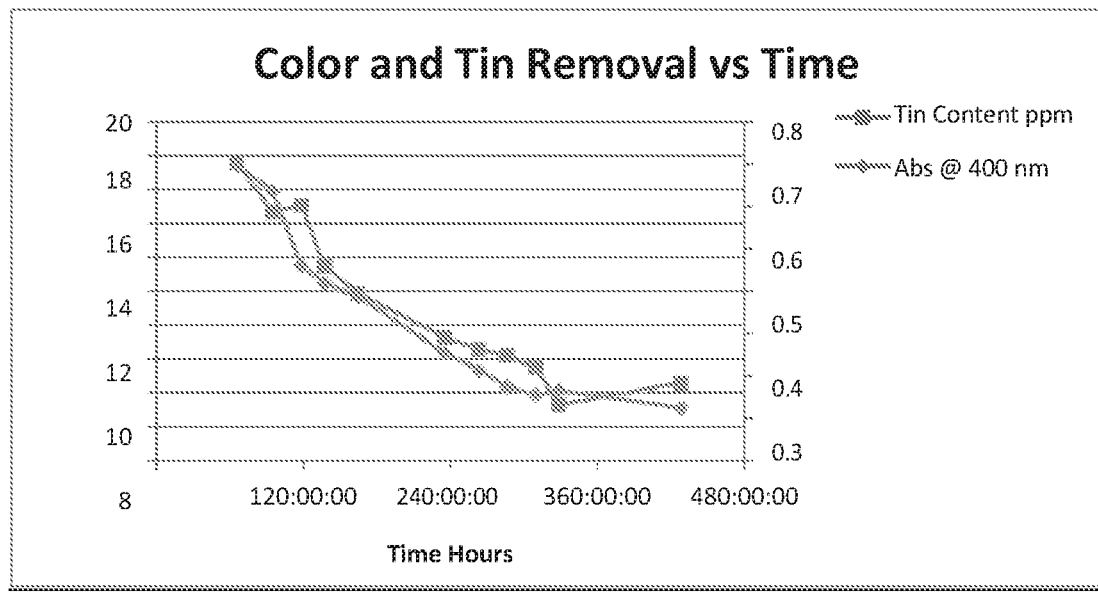

PURIFICATION AND DECOLORIZATION OF POLYMERS

CROSS-REFERENCE TO RELATED APPLICATION

This application a national stale application under 35 U.S.C. § 371 of PCT Application No. PCT/US2017/015095, having an international tiling date of 26 Jan. 2017, which designated the United States; which PCT application claimed the benefit of U.S. Provisional Patent Application 62/288,782, filed 29 Jan. 2016, both of which are incorporated herein by reference in their entirety.

FIELD OF THE INVENTION

The invention pertains to the purification and decolorization of polymers, and particularly to the removal of catalysts, such as metal catalysts, and organic impurities, such as colored decomposition products and/or glycolide derivatives, from polymer solutions.

BACKGROUND OF THE INVENTION

Polymers, including but not limited to linear polymers and star polymers, particularly those comprising one or more monomers selected from the group consisting of ethylene glycol, lactide, glycolate, glycolide, and caprolactone, have found use as delivery vehicles for small-molecule drugs. Particularly, the small molecule may be entrapped within the polymer structure, and the drug may be released into a patient's body gradually over an extended period of time following administration of the polymer formulation to the patient.

During the synthesis of a polymer, particularly when the synthesis is initiated by a reducing sugar or a sugar alcohol and/or catalyzed by, e.g., a tin catalyst, decomposition byproducts typically form and may be present in a mixture with the polymer. The presence of such decomposition byproducts may result in the polymer mixture having a color, particularly a brownish color, rather than being clear or white. Polymers containing glycolides may also have an undesirable color, particularly a brown color. The presence of these impurities is generally undesirable, particularly in polymer compositions intended for parenteral administration to a patient, because the impurities may cause irritation to the patient or may interfere with intended release characteristics of the drug from the polymer delivery vehicle. There is thus a need in the art to effectively remove these impurities.

European Patent 469,520, entitled "Polylactide preparation and purification," issued 5 Feb. 1992 to Prikoszovich ("Prikoszovich"), discloses a method for the purification and color removal of glucose-initiated star polymers comprising lactide and glycolide monomers and is incorporated herein by reference in its entirety. In the method disclosed by Prikoszovich, a solution of the star polymer in, e.g., acetone is combined with activated charcoal and allowed to remain in contact with the activated charcoal for a period of time before being filtered. Prikoszovich discloses that a brown solution of a lactide/glycolide star copolymer was rendered colorless and had very low levels of tin catalyst after treatment by the disclosed method.

Attempts by the present inventors to reproduce the results described by Prikoszovich revealed several problems inherent in the method of Prikoszovich. Fine carbon particles utilized in the polymer solution rapidly clogged the filters, even when filters with large surface areas were used; this problem was only partially mitigated by the use of granulated carbon.

The present inventors attempted to modify the method of Prikoszovich by loading granular activated carbon into stainless steel pipes to form a carbon bed and slowly recirculating the polymer solution through the carbon bed. Although this modification was successful in preventing carbon fines from clogging the filter and in removing color and tin catalyst from the polymer solution, the modified method was complicated and unreliable, required long circulation times and large quantities of activated carbon, and generated large quantities of flammable spent solvent.

Additionally, when metal catalysts are employed in polymer synthesis methods, the resulting polymer is often covalently bonded or otherwise tightly bound to the metal catalyst, which may be problematic when the polymer is intended for administration to a patient due to the potential toxicity of the metal catalyst. There is thus a need in the art to remove metal catalysts, including but not limited to tin catalysts, from solutions of polymers, especially from polymer solutions intended for administration to a patient.

It is therefore advantageous to develop a method for purification, and particularly for decolorization and/or catalyst removal, of polymer solutions, including but not limited to solutions of linear polymers and star polymers, that is simpler, more reliable, more efficient, and safer than the methods of the prior art. It is further advantageous to develop such a method that is suitable in scale to purify large quantities of polymer solution to a very high level of purity, as may be appropriate, by way of non-limiting example, for polymer solutions intended for parenteral administration to a patient. It is still further advantageous to develop methods that effectively remove metal catalysts, including but not limited to tin catalysts, from polymer solutions, whereby metal removal may be performed separately from or in conjunction with decolorization.

SUMMARY OF THE INVENTION

The invention provides a method for decolorization of a polymer composition comprising a polymer and a solvent, comprising (a) adding a photocatalyst to the polymer composition, and (b) exposing the polymer composition to ultraviolet (UV) light to remove color from the polymer composition.

The invention also provides method for preparing a polymer composition comprising a polymer and a solvent, comprising (a) adding a metal scavenger to the polymer composition to form a complex with a metal contaminant in the polymer composition; (b) separating the metal scavenger and metal contaminant complex from the polymer; (c) adding a photocatalyst to the polymer composition; (d) exposing the polymer composition to ultraviolet (UV) light to remove color from the polymer composition; and (e) separating the photocatalyst from the polymer composition.

The invention further provides a method for preparing a polymer composition comprising a polymer and a solvent, comprising (a) adding a metal scavenger to the polymer composition to form a complex with a metal contaminant in the polymer composition; and (b) separating the metal scavenger and metal contaminant complex from the polymer, wherein the metal scavenger is a metal scavenger chelating agent.

The invention still further provides a method for preparing a pharmaceutical composition, comprising (a) treating a polymer composition comprising a polymer and a solvent to reduce an amount of a metal contaminant in the polymer composition; and (b) combining the polymer composition with a peptide- or protein-based pharmaceutical agent.

These and other advantages and embodiments of the present invention will be apparent to those skilled in the art from the following Description of the Invention.

BRIEF DESCRIPTION OF THE DRAWING

FIG. 1 is a graph illustrating removal of color and tin catalyst from a star polymer solution as functions of time, by a method according to the present invention.

DESCRIPTION OF THE INVENTION

As used herein, the term "agitation" refers to the actuation or putting into motion of a fluid continuously for a period of time so as to induce turbulent flow in the fluid. Examples of methods for agitating a fluid include, but are not limited to, shaking and stirring.

As used herein, the term "branch point" refers to a location in a branch polymer at which one or more chains are covalently bonded to a separate chain.

As used herein, the term "branched polymer" refers to a polymer in which a substituent of at least one monomer unit is replaced by a covalent bond to a side chain. Relative to the monomer unit to which it is bonded, the side chain may comprise monomer units of the same monomer, one or more different monomers, or combinations thereof. Examples of branched polymers include, but are not limited to, brush polymers, comb polymers, dendrimers, graft polymers, polymer networks, and star polymers.

As used herein, the term "brush polymer" refers to a branched polymer comprising a single main chain and at least three linear, unbranched side chains, wherein at least three side chains are covalently bonded to the main chain at a single branch point.

As used herein, the terms "chelating agent" and "metal scavenger chelating agent" are interchangeable and each refer to a material that, when added to a solution comprising a metal, forms at least two separate coordinate bonds with an atom of the metal, so as to sequester the metal and thereby allow the metal to be removed from the solution. Unless otherwise specified, activated carbon is not a "chelating agent" or "metal scavenger chelating agent" as defined herein.

As used herein, the term "comb polymer" refers to a branched polymer comprising a single main chain and at least four linear, unbranched side chains, wherein at least two side chains are covalently bonded to the main chain at each of at least a first branch point and a second branch point. As used herein, the term "regular comb polymer" refers to a comb polymer in which all side chains are identical.

As used herein, the term "dendrimer" refers to a branched polymer with many levels of branching, i.e. in which a side chain may have a branch point with a side chain, which in turn has a branch point with another side chain, which in turn has a branch point with another side chain, etc. Dendrimers are distinguished from polymer networks in that dendrimers comprise few crosslinks. As used herein, the term "first-generation dendrimer branch" refers to a side chain of a dendrimer that is bonded to a central core or main chain of the dendrimer; the term "second-generation dendrimer branch" refers to a side chain of a dendrimer that is not a first-generation dendrimer branch but is bonded to a first-generation dendrimer branch; the term "third-generation dendrimer branch" refers to a side chain of a dendrimer that is not a first- or second-generation dendrimer branch but is bonded to a second-generation dendrimer branch; and so on.

As used herein, the term "graft polymer" refers to a branched polymer in which a structure or configuration of a side chain is different from a structure or configuration of the main chain.

As used herein, the terms "linear" and "unbranched" are interchangeable, each referring to any polymer chain or molecule that does not comprise a branch point.

As used herein, the term "linear polymer" refers to a polymer that is not a branched polymer.

As used herein, the term "metal scavenger" refers to any material that reacts with, traps, or otherwise removes metals from a solution. Examples of metal scavengers include, but are not limited to, activated charcoal and metal scavenger chelating agents.

As used herein, the term "polymer network" refers to a branched polymer in which many chains are bonded to many other chains, i.e. a branched polymer comprising many crosslinks.

As used herein, the term "star polymer" refers to a branched polymer in which at least two linear, unbranched side chains are bonded to a central core or main chain at a single branch point. As used herein, the term "regular star polymer" refers to a star polymer in which each side chain is identical. As used herein, the term "variegated star polymer" refers to a star polymer in which two side chains bonded to the central core or main chain at the same branch point each comprise a different structure, configuration, or pattern of monomer units.

As used herein, the terms "simultaneous" and "substantially simultaneous" are interchangeable, each referring to events that occur at approximately the same time or that both occur prior to another identified event. By way of non-limiting example, process steps that are performed "simultaneously" or "substantially simultaneously" are those that are performed at approximately the same time, or that are both performed prior to another identified process step.

As used herein, the terms "ultraviolet light" and "UV light" are interchangeable, each referring to light having a wavelength of between about 100 nanometers and about 450 nanometers. As used herein, the term "UVA light" refers to ultraviolet light having a wavelength of between about 315 nanometers and about 400 nanometers.

The present invention provides methods for decolorization of solutions of polymers, including but not limited to star polymers, in organic solvents. The methods of the present invention are particularly useful for decolorizing solutions of polymers that contain glycolides, or that are synthesized by methods initiated by a reducing sugar such as glucose. According to methods of the present invention, a photocatalyst, e.g. titanium dioxide ($TiO_2$), is added to a polymer composition that comprises a polymer and a solvent, which is then exposed to ultraviolet (UV) light to remove color from the polymer composition. The methods of the present invention result in a substantial reduction of color in both the solution and the polymer itself after the polymer is separated from the solution, while also having the surprising and unexpected advantage of not affecting critical polymer attributes, such as composition, molecular weight, polydispersity, or acid value.

Any photocatalyst that catalyzes the degradation of non-polymeric organic compounds in the presence of UV light may be utilized in the decolorization methods of the present invention. Photocatalysts suitable for use in the decolorization methods of the present invention preferably have a band gap of at least about 3.0 eV, and even more preferably at least about 3.2 eV. Preferred photocatalysts may comprise, by way of non-limiting example, titanium dioxide and zinc oxide. Titanium dioxide photocatalysts, particularly those comprising the anatase and/or rutile polymorphs of titanium dioxide, are especially preferred. A preferred titanium dioxide photocatalyst comprises anatase and rutile in a mass ratio of anatase to rutile of between about 1:9 and about 9:1, even more preferably between about 7:3 and about 4:1. To provide for easier removal of the photocatalyst by filtration after the decolorization has been performed, the photocatalyst preferably has a particle size of more than 0.2 micrometers, and even more preferably of more than 1 micrometer, but commercially available titanium dioxide catalysts having good photocatalytic activity and smaller particle sizes, such as Evonik Industries AEROXIDE® p25 catalyst, may also be used.

Any solvent in which the polymer of interest is soluble is suitable for use in the methods of the present invention, and those of ordinary skill in the art will understand how to choose an appropriate solvent for the particular polymer to be decolorized and/or otherwise purified. Most typically, the solvent will be a polar solvent. Example of solvents suitable for use in the methods of the present invention include, but are not limited to, ketones (including but not limited to acetone), alcohols (including but not limited to ethanol and propylene glycol), water, acetonitrile, tetrahydrofuran, methylene chloride, chloroform, and ethyl acetate.

Any colored polymer that is not significantly degraded by the photocatalysis procedures disclosed herein may be decolorized by the methods of the present invention. Polymers that may require decolorization include those that are synthesized using a reducing sugar, such as glucose, or a sugar alcohol, such as mannitol, as an initiator. Such reducing sugar or sugar alcohol initiators may degrade in the presence of heat and/or catalyst, resulting in the production of dark-brown color bodies that may become incorporated into the polymer. Polymers that contain appreciable quantities of glycolide may also have an undesirable color that can be decolorized by the methods of the present invention. The decolorization methods of the present invention may, but need not, be applied particularly to polymers useful as drug delivery vehicles. Examples of polymers useful as drug delivery vehicles include, but are not limited to, polymers comprising one or more monomers selected from the group consisting of methacrylate, ethylene glycol, lactide, glycolate, glycolide, and caprolactone.

Those of ordinary skill in the art will understand how to choose an appropriate wavelength of UV light for the particular photocatalyst used in the decolorization methods of the present invention. By way of non-limiting example, the rutile polymorph of titanium dioxide is irradiated at wavelengths of 413 nanometers or less, and the anatase polymorph is irradiated at wavelengths of 388 nanometers or less. In some embodiments, the UV light has a wavelength between about 100 nanometers and about 450 nanometers, between about 200 nanometers and about 450 nanometers, or between about 300 nanometers and about 450 nanometers. In another embodiment, the UV light has a wavelength between about 315 nanometers and about 400 nanometers.

The step of exposing a polymer composition to UV light to remove color from the polymer composition can be conducted in a suitable manner to allow sufficient exposure of the polymer composition to the UV light so that the composition is decolorized. In some embodiments, the step of exposing comprises agitating the composition, which can be accomplished by methods known in the art. The step of exposing is conducted for suitable times to achieve desired degrees of decolorization. For example, the step of exposing can be conducted for at least about 10 hours, about 20 hours, about 30 hours, about 40 hours, about 50 hours, about 60 hours, about 70 hours, about 80 hours, about 90 hours, about 100 hours, about 125 hours, about 150 hours, about 175 hours, about 200 hours, about 225 hours, or about 250 hours. The step of exposing the polymer composition to UV light can be conducted in vessel made of a UV-transparent material, such as, by way of non-limiting example, glass and the source of UV light is shined at the vessel from the outside. Alternatively, the step of exposing the polymer composition to UV light can be conducted in any type of suitable vessel and the source of UV light can be positioned inside the vessel so that UV light is shined at the polymer composition from inside the vessel.

The method of decolorization of the present invention is effective at reducing color in both a polymer composition, e.g., a polymer solution, and in a polymer material recovered from a polymer composition. As described herein, some polymer compositions are brown or dark brown and can be decolorized to achieve either a clear or white color. There are various formal color scales known in the art that are suitable to quantify these changes. For example, the United States Pharmacopeia provides a color scale at USP Monograph 631, "Color and Achromicity." Alternatively, the European Pharmacopeia provides a color scale at Section 2.2.2. In some embodiments, the polymer composition and/or a recovered polymer material has a color of about USP T, about USP S, about USP R, about USP Q, about USP P, about USP O, about USP N, about USP M, about USP L, or about USP K on the United States Pharmacopeia color scale, or about $B_1$, about $B_2$, about $B_3$, about $B_4$, about $BY_1$, about $BY_2$, about $BY_3$, about $Y_1$, about $Y_2$, or about $Y_3$ on the European Pharmacopeia color scale, prior to the method of the present invention. In these and other embodiments, the polymer composition and/or a recovered polymer material has a color of about USP A, about USP B, about USP C, about USP D, about USP E, about USP F, about USP G, about USP H, about USP I, or about USP J on the US Pharmacopeia color scale, or about $Y_7$, about $Y_6$, about $Y_5$, about $BY_7$, about $BY_6$, about $BY_5$, about $B_9$, about $B_8$, about $B_7$, or about $B_6$ on the European Pharmacopeia color scale after practice of the method of the present invention. The polymer composition and/or a recovered polymer material, in some embodiments, may be substantially colorless.

The color of the polymer composition and/or a recovered polymer material before, during, or after the decolorization method of the present invention can also be quantified by UV-visual spectroscopy, i.e. by measuring the absorbance of a solution of the polymer at a UV or visual wavelength of light. Those of ordinary skill in the art will understand an appropriate wavelength of light for use in UV-visual spectroscopic characterization of the color of the polymer composition and/or recovered polymer. By way of non-limiting example, an appropriate wavelength for UV-visual spectroscopy in characterizing the color of the polymer composition and/or recovered polymer obtained by the present invention may be between about 320 nanometers and about 400 nanometers. By way of further non-limiting example, a polymer solution having a very dark brown color may have an absorbance at 320 nanometers of more than about 1.7; a polymer solution having a mid-dark brown color may have an absorbance at 320 nanometers of between about 0.82 and about 1.7; a polymer solution having a yellow or tan color may have an absorbance at 320 nanometers of between about 0.155 and about 0.82; and a substantially colorless polymer may have an absorbance at 320 nanometers of less than about 0.155.

This embodiment of the invention can further include the step of separating the photocatalyst from the polymer composition. For example, the photocatalyst can be removed by any suitable method, including by centrifugation, decantation or filtration.

In another embodiment, the present invention provides methods for preparing a polymer composition comprising a polymer and a solvent by removing metal contaminants, such as metal catalysts, such as, by way of non-limiting example, tin(II) catalysts, from the polymer composition, including but not limited to star polymer compositions. Methods for removing a metal contaminant from a polymer solution according to the present invention add a metal scavenger to a polymer composition that comprises a polymer and a solvent to form a complex with a metal contaminant in the polymer composition. The methods further include separating the metal scavenger and metal contaminant complex from the polymer. Such metal removal methods of the present invention may, when performed before or during decolorization, improve the efficiency of the decolorization methods of the present invention, and may also improve the biocompatibility of colored or colorless polymer solutions by removing potentially toxic metals.

In this embodiment, the step of adding a metal scavenger to the polymer composition can comprise adding the metal scavenger to the polymer composition in two or more aliquots. It has been found that the use of multiple aliquots of a metal scavenger increases the efficiency of metal removal. The total number of aliquots can be 2, 3, 4, 5, 6, 7, 8, 9 or 10. When the metal scavenger is added in two or more aliquots, the amount of the total metal scavenger in an aliquot can range in whole number increments from 10%-90% of the total, and the total amount can be evenly divided between the number of aliquots or not. The aliquots can be added at even or irregular time intervals throughout the process, and such time intervals can be from 1 to 100 hours, in whole number increments. Further, when the metal scavenger is added in two or more aliquots, a complex of the metal contaminant and the metal scavenger can be removed after addition of one aliquot and before addition of the subsequent aliquot, preferably, immediately before the subsequent aliquot.

Metal contaminants in polymer compositions are typically metal catalysts used in the preparation of the polymer. Such metal contaminants can be selected from aluminum, gallium, tin, and bismuth. In some embodiments, the contaminant is divalent tin and can be selected from tin(II) 2-ethylhexanoate, tin(II) bromide, tin(II) chloride, tin(II) fluoride, tin(II) hydroxide, tin(II) iodide, tin(II) oxide, tin selenide, tin(II) sulfate, tin(II) sulfide, and tin telluride.

Metal removal methods of the present invention utilize a metal scavenger, such as activated charcoal or a metal scavenger chelating agent, in some embodiments an acidic metal scavenger chelating agent. The metal scavenger is preferably in the solid phase, which permits removal of both the metal scavenger and the metal from the polymer solution by filtration. Solid-phase metal scavengers may, but need not, be bound to a polymer or silica. Examples of metal scavengers suitable for use in the present invention include, but are not limited to, polymer-bound ethylenediaminetriacetic acid acetamide and Sigma Aldrich QuadraPure® metal scavengers. Preferred metal scavengers may also include, by way of non-limiting example, SiliCycle SiliaMetS® scavengers, such as SiliaMetS® Cysteine or SiliaMetS® TAAcOH. Solid-phase acidic reagents, such as SiliCycle SiliaBond® Carboxylic Acid, may also be used, alone or in combination with non-acidic solid-phase metal scavengers, such as SiliaMetS® TAAcONa or SiliaMetS® Cysteine.

The step of separating a complex of a metal scavenger and a metal contaminant can be conducted by any suitable process or method, including by centrifugation, decantation, or filtration.

The method of preparing a polymer composition by metal removal can further include the step of recovering the polymer from the polymer composition. For example, the polymer can be precipitated from the polymer composition and optionally, dried.

Methods of the present invention for metal removal are highly effective. In some embodiments, prior to removal of metals, the concentration of metal contaminants can be greater than about 450 ppm, about 600 ppm, about 750 ppm, about 900 ppm, about 1050 ppm, about 1200 ppm, about 1350 ppm, about 1500 ppm, about 1650 ppm, or about 1800 ppm. In other embodiments, prior to removal of metals, the concentration of metal contaminants can be less than about 2000 ppm, about 1600 ppm, about 1200 ppm, about 800 ppm, about 400 ppm, about 300 ppm, about 200 ppm, about 100 ppm, about 75 ppm, or about 50 ppm. In those and other embodiments, after removal of metals, the concentration of metal contaminants can be less than about 50 ppm, about 40 ppm, about 20 ppm, about 19 ppm, about 18 ppm, about 17 ppm, about 16 ppm, about 15 ppm, about 14 ppm, about 13 ppm, about 12 ppm, about 11 ppm, about 10 ppm, about 9 ppm, about 8 ppm, about 7 ppm, about 6 ppm, about 5 ppm, about 4 ppm, about 3 ppm, about 2 ppm, or about 1 ppm. In other embodiments, the amount of metal contaminant in a polymer composition after the method compared to the amount of metal contaminant before the method is no more than about 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%.

Metal removal methods of the present invention are particularly applicable to solutions of polymers intended for use as drug delivery vehicles where the drug to be administered to a patient is a peptide or protein. Metal catalysts, particularly tin catalysts, left over in the polymer when the polymer is combined with the peptide or protein drug may cause acylation of the peptide or protein, which may make the peptide or protein therapeutically ineffective or even toxic to the patient. This risk has generally been left unaddressed by the methods of the prior art, which typically do not attempt to remove metal catalysts left over in the polymer solution. Accordingly, another embodiment of the present invention is a method for preparing a pharmaceutical composition that is substantially free of metal catalysts, such as tin catalysts, to prevent possible acylation of a protein or peptide drug. Such method includes treating a polymer composition comprising a polymer and a solvent to reduce the amount of metal contaminant in the polymer composition. The step of treating can include adding a metal scavenger to the polymer composition to form a complex with the metal contaminant and separating the complex from the polymer. After the complex is removed, the polymer is combined with a peptide- or protein-based pharmaceutical agent to formulate a pharmaceutical composition.

Another embodiment of the present invention is a method to decolorize and to remove a metal contaminant from a polymer composition comprising a polymer and a solvent. The method includes (i) adding a metal scavenger to the polymer composition to form a complex with a metal contaminant in the polymer composition, and separating the metal scavenger and metal contaminant complex from the polymer; and (ii) adding a photocatalyst to the polymer composition, exposing the polymer composition to ultraviolet (UV) light to remove color from the polymer composition, and separating the photocatalyst from the polymer composition. The method can further include recovering the polymer from the polymer composition, such as by precipitating the polymer from the composition and optionally, further drying the polymer.

In this embodiment, the steps of sub-process (i) can be conducted prior to the steps of sub-process (ii). Alternatively, the steps of sub-process (i) and the steps of sub-process (ii) can be conducted substantially simultaneously or the steps of sub-process (ii) can be conducted prior to the steps of sub-process (i). If decolorization and metal catalyst removal are performed simultaneously, the polymer solution is combined with the photocatalyst and a metal scavenger before exposure to the UV light. Alternatively, the polymer solution may be pre-treated with a metal scavenger, and preferably filtered, before being combined with the photocatalyst. In certain embodiments, the metal removal methods of the present invention may also be performed separately from or instead of decolorization, as in the case of a substantially colorless solution.

The invention is further illustrated by the following non-limiting examples.

Comparative Example 1

Decolorization of a Star Polymer by Method According to Prikoszovich 10 grams of glucose-initiated lactide/glycolide star copolymer was dissolved in 150 milliliters of acetone and filtered to remove insoluble material. The resulting brown solution was combined with 10 grams of Fisher Scientific Fisherbrand™ Activated Carbon Charcoal, 50 to 200 mesh, then stirred for three hours. The solution was then filtered using Imerys Filtration Minerals CELITE® HyFlo™ filter aid with paper and glass fiber filter media. After initial filtration, a significant quantity of carbon fines remained in solution; these fines were removed using pressure filtration and a 0.2 micrometer PTFE capsule filter. The resulting brown solution was dried under nitrogen gas, re-dissolved in dichloromethane, and precipitated into methanol. The yielded polymer still had an unacceptable brown color, and the present inventors surmised that the carbon material was ineffective at decolorizing the polymer.

Comparative Example 2

Decolorization of a Star Polymer by Method According to Prikoszovich

Approximately 10.3 grams of glucose-initiated lactide/glycolide star copolymer was dissolved in 100 milliliters of acetonitrile. The resulting dark brown solution was combined with 1.5 grams of Cabot NORIT® SX-2 activated charcoal powder, then agitated for 21 hours. The solution was then filtered through a series of filters of decreasing pore size to remove the carbon fines: a 0.7-micrometer glass microfiber filter, then a 0.45-micrometer PTFE filter, and finally a 0.2-micrometer FTFE filter. The resulting solution was almost completely colorless, and the dried polymer yielded was a colorless solid. However, the polymer was difficult to filter, as the series of filters of decreasing pore size was necessary to overcome filter clogging problems.

Comparative Example 3

Decolorization of a Star Polymer by Modified Method According to Prikoszovich

Approximately 444 grams of glucose-initiated lactide/glycolide star copolymer was dissolved in 4000 milliliters of acetonitrile. The resulting dark brown solution was recirculated, by a peristaltic pump with PTFE tubing, through a total of five preloaded Whatman Carbon Cap 150 carbon capsules at a rate of 5-25 milliliters per minute. The solution was then filtered through 5-micrometer and 1-micrometer polypropylene capsule filters. The resulting filtered solution was light yellow in color, and the dried polymer yielded was a colorless solid.

While this modification to the method of Prikoszovich effectively eliminated the filter clogging problem of Comparative Example 2, the modified method required long circulation times and large quantities of activated carbon.

Example 1

Removal of Color and Metal from a Star Polymer According to the Present Invention To establish a standard by which polymer color could be evaluated and compared in the following two Examples, 1.11 grams of dried polymer of varying visually observable color from each of the above Comparative Examples was dissolved in 10 milliliters of acetonitrile and filtered with a 0.7-micrometer glass microfiber filter. The UV absorbance of the solutions in the range of 320-400 nanometers was determined using a Beckman Coulter DU 720 Spectrophotometer, and was found to correlate well with polymer solution color, as shown in Table 1.

TABLE 1

Solution color determination by UV-visible spectrophotometry

| Dried polymer color | Solution color | Absorbance at ~320 nm |
| --- | --- | --- |
| Very dark | Very dark | >2.0 (detector saturated) |
| Mid-dark | Mid-dark | 1.4 |
| Light yellow/tan | Light yellow/tan | 0.24 |
| Colorless | Colorless | 0.07 |

5790 grams of very dark brown glucose-initiated lactide/glycolide star copolymer was dissolved in 34 liters of acetonitrile in a 50-liter glass reactor and stirred. To the stirred solution, 86.9 grams of anatase (325 mesh), 28.9 grams of rutile (particle size 5 micrometers or less), and 521 grams (three stoichiometric equivalents of the theoretical tin content) of SiliaMetS® TAAcOH were added. The solution was rapidly stirred and exposed to three 400-watt metal halide bulbs emitting UV light for 428.5 hours; after seven days of stirring and UV exposure, another aliquot of 174 grams (two stoichiometric equivalents of the theoretical tin content) of SiliaMetS® TAAcOH was added.

Samples of the solution were taken at various times to record various polymer attributes, including UV-visual absorbance at 400 nanometers, relative molecular weight, and tin and titanium content. Molecular weight was measured by size exclusion chromatography (SEC) in chloroform with polystyrene standards, and tin and titanium content were measured by inductively coupled plasma mass spectrometry (ICP-MS). UV-visual analysis was performed on the filtered solution, while SEC and ICP-MS samples were concentrated, precipitated from a methanol/water mixture, and dried prior to analysis. The results are given in Table 2 and illustrated in FIG. 1; as shown in Table 2, the critical polymer attributes of molecular weight and polydispersity were not appreciably altered by the decolorization and metal removal processes, but the tin and color were effectively removed.

TABLE 2

Star polymer attributes during purification process

| Sample | Mol. wt.* | Poly-dispersity | Titanium (ppm) | Tin (ppm) | UV-vis. abs. @ 400 nm | Rxn time (hr:min) |
|---|---|---|---|---|---|---|
| Initial | 100.0 | 5.68 | ND | 1817 | ND | n/a |
| 1 | 100.2 | 3.91 | 1.8 | 17.6 | 0.699 | 65:45 |
| 2 | 100.3 | 4.10 | 9.2 | 14.7 | 0.638 | 94:13 |
| 3 | 100.3 | 4.21 | 3 | 15.1 | 0.462 | 117:40 |
| 4 | 102.0 | 4.46 | 1.6 | 11.5 | 0.420 | 137:00 |
| 5 | 102.2 | 4.34 | 6.5 | 9.9 | 0.388 | 164:03 |
| 6 | 102.8 | 4.39 | 6.9 | 7.3 | 0.255 | 235:02 |
| 7 | 102.6 | 4.50 | 5.9 | 6.6 | 0.215 | 263:15 |
| 8 | 104.7 | 4.38 | 4.2 | 6.2 | 0.175 | 286:00 |
| 9 | 100.5 | 4.24 | 4.3 | 5.5 | 0.156 | 309:24 |
| 10 | 101.4 | 4.37 | 4.8 | 3.3 | 0.166 | 328:33 |
| 11 | 101.8 | 4.79 | 0.3 | 4.6 | 0.125 | 428:33 |
| Final | 96.1 | 4.31 | 0.6 | 4.2 | ND | n/a |

*Percent, relative to initial polymer

After UV-visual color determination indicated that the decolorization was complete (absorbance of no more than 0.18 at 400 nanometers), the polymer solution was nitrogen pressure-filtered using a 0.2-micrometer PTFE cartridge filter. The clear, light yellow solution was concentrated in vacuo to approximately 24 liters and precipitated into a methanol-water mixture. The complete process yielded 5049.3 grams of dried, purified, colorless polymer.

As measured by gel permeation chromatography (GPC), a drop of approximately 4% in molecular weight occurred during the drying process. As determined by $^1$H nuclear magnetic resonance (NMR) spectroscopy, 0.36% of the original lactide and 0.00% of the original glycolide remained as residual monomer.

Example 2

Removal of Color and Metal from a Linear Polymer According to the Present Invention Approximately 5 grams of a brown linear 1:1 lactide/glycolide copolymer was dissolved in 30 milliliters of acetonitrile. To this solution, 100 milligrams grams of anatase (325 mesh), 40 milligrams of rutile (particle size 5 micrometers or less), and 110 milligrams (4.5 stoichiometric equivalents of the theoretical tin content) of SiliaMetS® TAAcOH were added. The solution was stirred and exposed to a 400-watt metal halide bulb emitting UV light for approximately 22 hours.

Filtered samples of the solution were taken at 15 hours and at 21.75 hours to record the UV-visual absorbance at 400 nanometers; the initial and final samples were also tested for molecular weight by SEC and for tin and titanium content by ICP-MS. UV-visual analysis was performed on the filtered solution, while SEC and ICP-MS samples were concentrated, precipitated from a methanol/water mixture, and dried prior to analysis. The results are given in Table 4; as the Table shows, the critical polymer attributes of molecular weight and polydispersity were not appreciably altered by the decolorization and metal removal processes, but the tin and color were effectively removed.

TABLE 3

Linear polymer attributes during purification process

| Sample | Mol. wt.* | Poly-dispersity | Titanium (ppm) | Tin (ppm) | UV-vis. abs. @ 400 nm | Rxn time (hr:min) |
|---|---|---|---|---|---|---|
| Initial | 100 | 1.8 | 0.299 | 176.660 | 0.855 | n/a |
| 1 | ND | ND | ND | ND | 0.262 | 15:00 |
| Final | 108 | 2.0 | 2.365 | 74.499 | 0.165 | 21:45 |

A slight increase in molecular weight was observed in the purified polymer, which may be due to removal of a low-molecular weight fraction during precipitation.

Example 3

Removal of Metal from Star Polymer According to the Present Invention

Four experiments were performed on samples of a solution of glucose-initiated star polymer in acetonitrile having a concentration of approximately 0.3 grams of polymer per milliliter of solvent. In Experiments 1, 2, and 3, anatase and rutile in a mass ratio of 3:1 were added to the solutions, which were then exposed to UVA light and stirred in glass bottles for approximately 21 hours. In Experiment 4, which served as an activated carbon control experiment, the solution was recirculated through 50.7 grams of Norit® 12×20 Granular Activated Charcoal for approximately 48 hours in the absence of photocatalyst. Upon completion of the experiments, each solution was filtered with a 0.2-micrometer PTFE filter and precipitated from a methanol/water mixture. The results of all four experiments are given in Table 4.

TABLE 4

Results of tin removal experiments

| Experiment | Polymer sol'n wt. (g) | TiO$_2$ (w/w %) | SiliaMetS® TAAcONa (g) | Additive | Additive vol. (mL) | Sn reduction (%) |
|---|---|---|---|---|---|---|
| 1 | 151 | 1.5 | 3.0 | Acetic acid | 0.11 | 77 |
| 2 | 151 | 1.5 | 3.0 | IPA | 0.50 | 65 |
| 3 | 151 | 1.5 | 0 | Acetic acid | 0.11 | 26 |
| 4 | 151 | 0 | 0 | Acetic acid | 0.11 | 49 |

As shown in Table 4, the greatest reduction in tin content was observed in Experiment 1. The present inventors therefore speculate that a slightly acidic environment may improve the efficiency of the metal removal methods of the present invention. A follow-up experiment similar in design to Experiment 1, utilizing SiliaMetS® TAAcOH added to the same polymer solution as above and stirred for approximately 60 hours, yielded an 80% reduction in tin content after filtration and precipitation as explained above. SiliaMetS® TAAcOH, an acidic solid-phase chelation agent, was thus even more effective at removing tin from the polymer solution. The present inventors have thus discovered that a solid-phase chelation agent, optionally in conjunction with an acidic additive, increases metal removal efficiency significantly.

Various modifications of the above described invention will be evident to those skilled in the art. It is intended that such modifications are included within the scope of the following claims.

What is claimed is:

1. A method for preparing a polymer composition comprising a polymer and a solvent, comprising:
   (a) adding a metal scavenger to the polymer composition to form a complex with a metal contaminant in the polymer composition;
   (b) separating the metal scavenger and metal contaminant complex from the polymer;
   (c) adding a photocatalyst to the polymer composition;
   (d) exposing the polymer composition to ultraviolet (UV) light to remove color from the polymer composition; and
   (e) separating the photocatalyst from the polymer composition.

2. The method of claim 1, wherein the photocatalyst is selected from the group consisting of titanium dioxide and zinc oxide.

3. The method of claim 2, wherein the photocatalyst is titanium dioxide, wherein the titanium dioxide comprises at least one of anatase and rutile.

4. The method of claim 3, wherein a mass ratio of anatase to rutile in the titanium dioxide is between about 1:9 and about 9:1.

5. The method of claim 1, wherein the UV light has a wavelength of between about 100 nanometers and about 450 nanometers.

6. The method of claim 1, wherein the photocatalyst has a band gap of at least about 3.0 eV.

7. The method of claim 1, wherein prior to the step of adding the photocatalyst, the polymer composition has a color of about USP T, about USP S, about USP R, about USP Q, about USP P, about USP O, about USP N, about USP M, about USP L, or about USP K on the United States Pharmacopeia color scale, or a color of about $B_1$, about $B_2$, about $B_3$, about $B_4$, about $BY_1$, about $BY_2$, about $BY_3$, about $Y_1$, about $Y_2$, or about $Y_3$ on the European Pharmacopoeia color scale.

8. The method of claim 1, wherein after the exposing step, the polymer composition has a color of about USP A, about USP B, about USP C, about USP D, about USP E, about USP F, about USP G, about USP H, about USP I, or about USP J on the United States Pharmacopeia color scale, or a color of about $Y_7$, about $Y_6$, about $Y_8$, about $BY_7$, about $BY_6$, about $BY_5$, about $B_9$, about $B_8$, about $B_7$, or about $B_6$ on the European Pharmacopoeia color scale.

9. The method of claim 1, wherein the polymer is selected from the group consisting of a linear polymer, a branched polymer, a graft polymer, a star polymer, a comb polymer, a brush polymer, a polymer network, and a dendrimer.

10. The method of claim 1, further comprising recovering the polymer from the polymer composition.

11. The method of claim 1, wherein the amount of metal contaminant in the polymer composition before the step of adding the metal scavenger is greater than about 450 ppm.

12. The method of claim 1, wherein the amount of metal contaminant in the polymer composition after the step of separating the metal scavenger is less than about 20 ppm.

13. The method of claim 1, wherein the amount of metal contaminant in the polymer composition after the step of separating the metal scavenger is no more than about 1% of the amount of metal contaminant in the polymer composition before the step of adding the metal scavenger.

14. The method of claim 1, wherein the metal scavenger is selected from the group consisting of activated carbon and a metal scavenger chelating agent.

15. The method of claim 14, wherein the metal scavenger is a solid-phase metal scavenger.

16. The method of claim 14, wherein the metal scavenger consists of either an acidic metal scavenger chelating agent alone, or an acidic metal scavenger chelating agent and a non-acidic metal scavenger chelating agent.

17. The method of claim 1, further comprising combining the polymer composition with a pharmaceutical agent to form a pharmaceutical composition suitable for administration to a patient.

18. The method of claim 17, wherein the pharmaceutical agent is a peptide- or protein-based pharmaceutical agent.

* * * * *